United States Patent [19]
Garde et al.

[11] Patent Number: 5,983,133
[45] Date of Patent: Nov. 9, 1999

[54] IONTOPHORESIS SYSTEM WITH VOLTAGE STEP-UP CIRCUIT

[75] Inventors: Kenneth E. Garde, New Windsor, N.Y.; Ronald J. Flower, Lawrenceville, Ga.

[73] Assignee: Becton, Dickinson and Company, Franklin Lakes, N.J.

[21] Appl. No.: 08/939,692

[22] Filed: Sep. 29, 1997

[51] Int. Cl.[6] .................................................. A61N 1/30
[52] U.S. Cl. ................................................. 604/20; 607/72
[58] Field of Search ........................ 604/20–21; 607/59, 607/72, 152–153

[56] References Cited

U.S. PATENT DOCUMENTS

| | | | |
|---|---|---|---|
| 4,141,359 | 2/1979 | Jacobsen et al. | 128/172.1 |
| 4,734,090 | 3/1988 | Sibalis | 604/20 |
| 4,764,164 | 8/1988 | Sasaki | 604/20 |
| 4,997,418 | 3/1991 | DeMartini | 604/20 |
| 5,195,953 | 3/1993 | DeMartini | 604/20 |
| 5,498,235 | 3/1996 | Flower | 604/20 |
| 5,499,967 | 3/1996 | Teillaud et al. | 604/20 |
| 5,540,669 | 7/1996 | Sage, Jr. et al. | 604/290 |
| 5,645,526 | 7/1997 | Flower | 604/20 |
| 5,688,232 | 11/1997 | Flower | 604/20 |
| 5,693,024 | 12/1997 | Flower | 604/20 |
| 5,795,321 | 8/1998 | McArthur et al. | 604/20 |

*Primary Examiner*—Wynn Wood Coggins
*Assistant Examiner*—LoAn H. Thanh
*Attorney, Agent, or Firm*—Arthur D. Dawson

[57] ABSTRACT

A iontophoretic drug delivery apparatus and a corresponding method is provided. The apparatus includes a switched-capacitor DC—DC voltage converter to step up a supply voltage, and a current control circuit that draws current from the stepped-up voltage.

10 Claims, 5 Drawing Sheets

IONTOPHORESIS SYSTEM WITH VOLTAGE STEP-UP CIRCUIT

FIELD OF THE INVENTION

This invention is in the field of iontophoresis. In particular, the invention relates to stepping up a battery voltage using a switched-capacitor DC—DC converter, and using the stepped up voltage to power an iontophoretic circuit.

BACKGROUND OF THE INVENTION

Iontophoresis is the application of an electrical current to transport ions through intact skin. One particularly advantageous application of iontophoresis is the non-invasive transdermal delivery of ionized drugs or other therapeutic agents into a patient. This is done by applying low levels of current to a patch placed on the patient's skin, which forces the ionized drugs contained in the patch through the patient's skin and into his or her bloodstream.

Passive transdermal patches, such as those used to deliver nitroglycerin for angina pectoris, estradiol for hormone replacement, and nicotine to stop smoking, can only use a limited number of drugs because they work by diffusion. Iontophoresis advantageously expands the range of drugs available for transdermal delivery, including, for example, parenteral drugs (e.g., peptides). Further, because the amount of drug delivered is related to the amount of current applied, the drug delivery rate can be precisely controlled by controlling the current, unlike the passive transdermal patches. This allows for more rapid delivery (onset) and drug reduction (offset) in the patient.

When compared to drug delivery by needle injection, iontophoresis is non-evasive. Also, iontophoresis avoids the risks and inconvenience associated with IV (intravenous) delivery. In addition, when compared to oral ingestion of drugs, drug delivery by iontophoresis bypasses the GI tract, thus reducing side-effects such as drug loss, indigestion and stomach distress, and eliminating the need for swallowing the drug. Iontophoresis also avoids drug loss due to hepatic first pass metabolism by the liver that occurs when drugs are ingested.

Further, transdermal drug delivery by iontophoresis permits continuous delivery of drugs with a short half life and easy termination of drug delivery. Because iontophoresis is more convenient, there is a greater likelihood of patient compliance in taking the drug. Thus, for all of the above reasons, iontophoresis offers an alternative and effective method of drug delivery, and an especially useful method for children, the bedridden and the elderly.

An iontophoretic drug delivery system typically includes a current source, such as a battery and current controller, and a patch. The patch includes an active reservoir and a return reservoir. The active reservoir contains the ionized drug. The return reservoir typically contains a saline gel and collects ions emanating from the patient's skin when the drug is being delivered into the patient's skin. The patch also has two electrodes, each arranged inside the active and return reservoirs to be in respective contact with the drug and saline. The anode (positive electrode) and the cathode (negative electrode) are respectively electrically connected to the anode and cathode of the current source by electrical conductors. Either the anode or the cathode is arranged within the drug reservoir, depending on the charge of the ionized drug, and is designated the active electrode. The other electrode is arranged within the return reservoir, and is designated the return electrode.

When current from the current source is supplied to the active electrode, the drug ions migrate from the drug reservoir toward and through the skin of the patient. At the same time, ions flow from the patient's skin into the saline solution of the return reservoir. Charge is transferred into the return electrode and back to the current source, completing the iontophoretic circuit.

The electronic controller between the battery and the patch controls the amount of current delivered to the patch. The controller may control the drug delivery profile by controlling the delivered current so that drug delivery to the patient is accomplished at a constant or varying rate, or over a short, long or periodic time interval. This type of controller may require relatively complex electrical circuitry to meet the above requirements.

Iontophoretic drug delivery circuits may be powered directly by a multi-celled battery. (These types of circuits, however, are not admitted to be prior art with respect to the present invention by their mention in this Background section.) This approach, however, has a number of drawbacks. Although any given voltage can be attained by connecting an appropriate number of cells in series, each additional cell increases the weight and size of the resulting package, and increases the cost of the device.

DC—DC inductive-type converters may be used to step up a supply voltage to eliminate the need for a large stack of battery cells. Inductive-type DC—DC converters, however, include inductive components such as transformers which are relatively bulky, expensive, and heavy, and emit electromagnetic noise.

SUMMARY OF THE INVENTION

This invention advantageously provides an iontophoretic drug delivery system that operates using a small number of cells and which overcomes the aforementioned drawbacks of conventional controllers.

In one aspect of the invention, an apparatus for iontophoretic drug delivery is provided. This apparatus includes a controller, a switched-capacitor DC—DC voltage converter for stepping up an input voltage, and a current control circuit. The current control circuit controls an iontophoretic current from the voltage converter output in accordance with a controller output signal.

In another aspect of the invention, a method of iontophoretic drug delivery is provided. This method includes the steps of converting an input voltage to an output voltage greater than the input voltage using a switched-capacitor DC—DC converter, and controlling an iontophoretic current supplied from the output voltage.

BRIEF DESCRIPTION OF THE DRAWINGS

These and other features and advantages of this invention can best be understood by reference to the detailed description of the preferred embodiments set forth below taken with the drawings, in which.

DETAILED DESCRIPTION OF THE PREFERRED EMBODIMENTS

Figure 1:
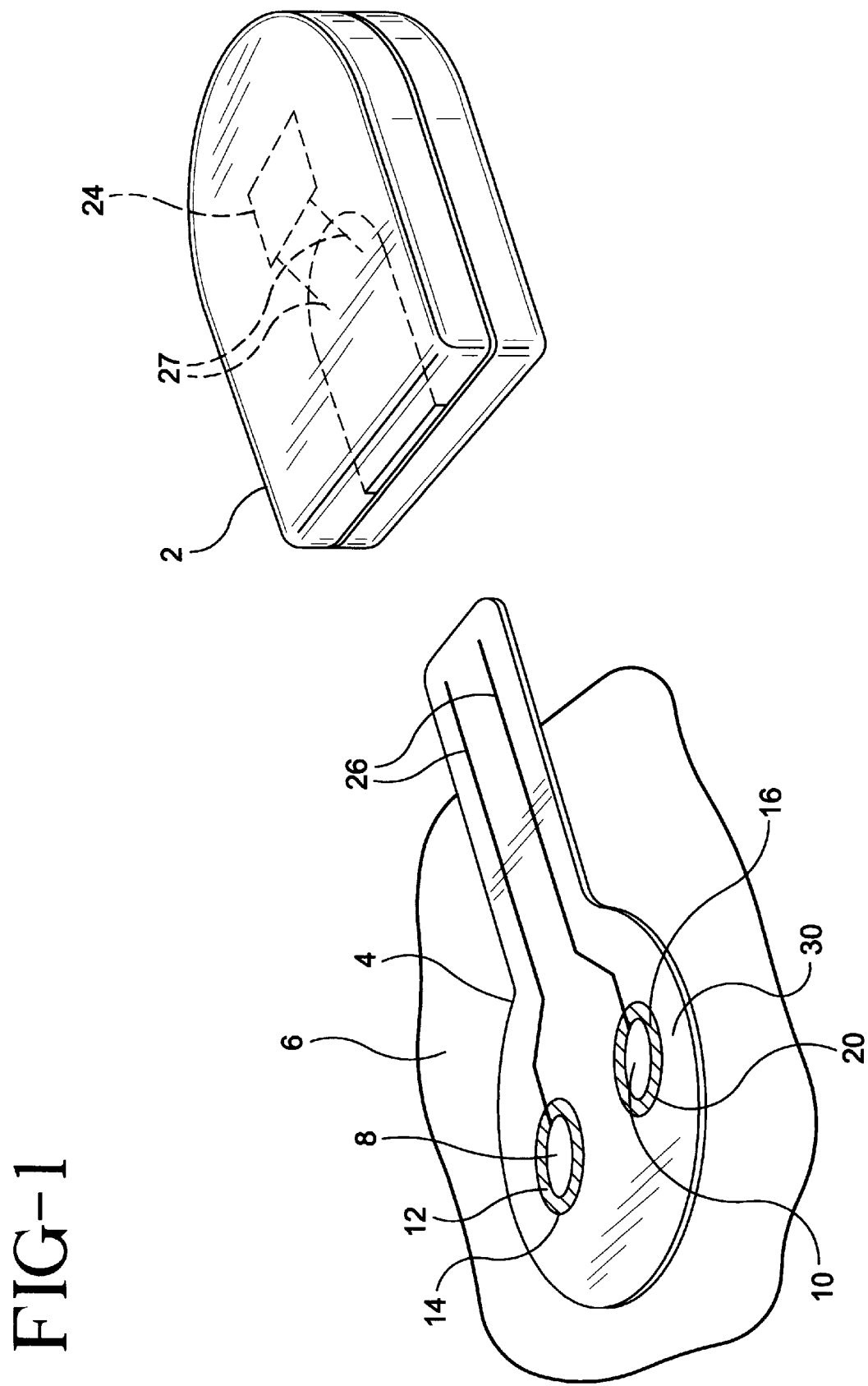
FIG. 1 is a perspective view of an iontophoretic drug delivery device of the present invention.

One suitable type of iontophoretic drug delivery device includes a separate, reusable electronic current controller 2, which can be removably and electrically connected to a patch 4 containing the drug, therapeutic agent or medicament, as shown in FIG. 1. The patch 4 is attached to the skin of the patient 6. The patch includes at least two electrodes, i.e., an active electrode 8 and a return electrode 10, with the ionic drug 12 and active electrode 8 positioned within the active reservoir 14, and the saline or electrolyte 16 and return electrode 10 positioned within the return reservoir 20.

The patch 4 is generally a planar flexible member formed of, for example, a biocompatible material such as woven or non-woven textiles or polymers, or any other construction well-known in the art. The patch is attached to the patient's skin using adhesives or a strap or both. In addition, it should be appreciated that the reservoirs 14, 20 may include a gel material which has sufficient tackiness to provide the necessary degree of adherence to the skin of the patient. The patch includes an enlarged patch body 30, which includes the active and return reservoirs.

Figure 2:
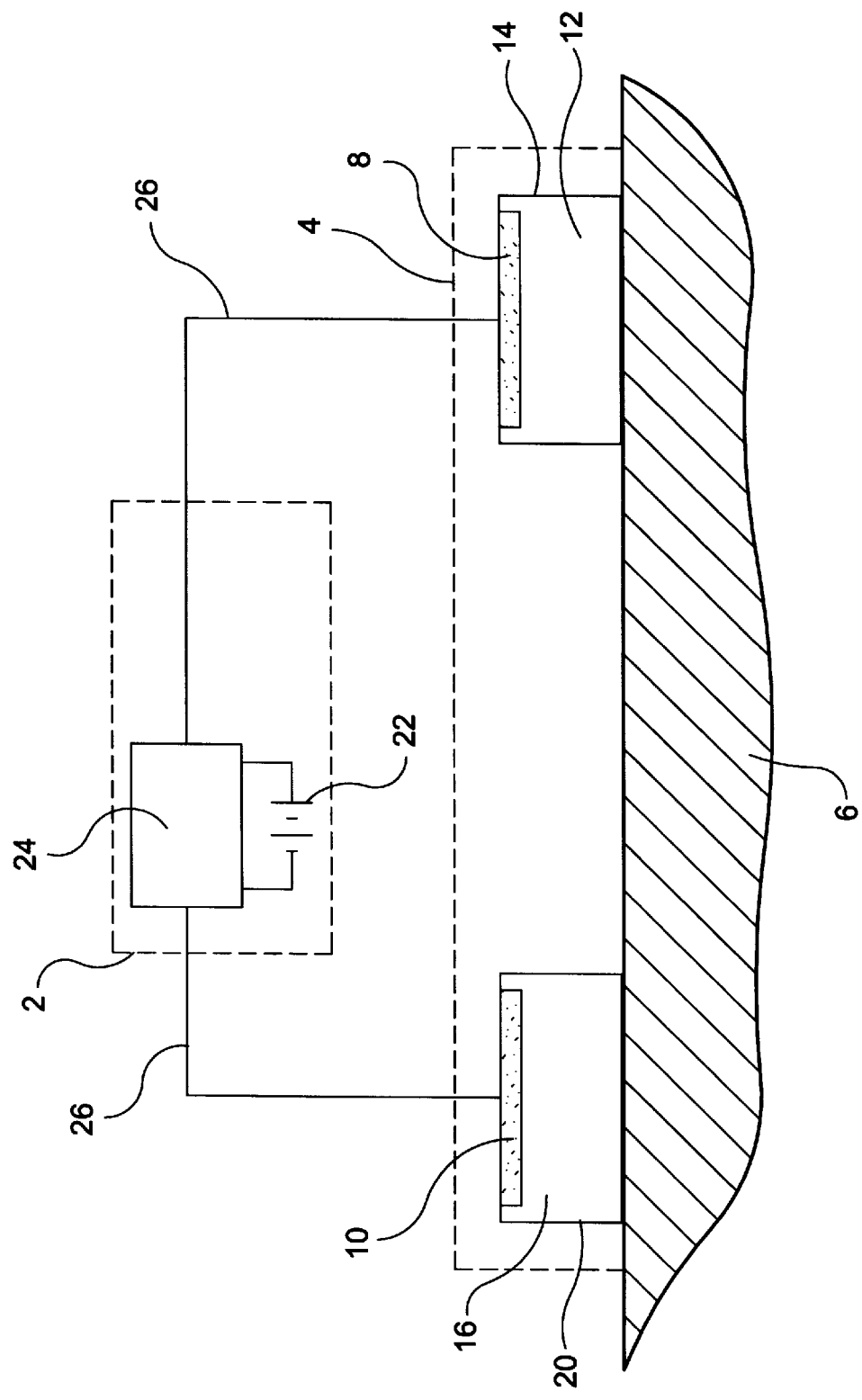
FIG. 2 is a high-level block diagram of the iontophoretic drug delivery device.

The iontophoretic drug delivery device also includes a controller 2 having a power source 22 and electronic control circuitry 24, as shown in FIG. 2. The controller 2 is electrically coupled to the patch 4 using electronic interconnectors 26, and 27 such as a printed flexible circuit, metal foils, wires, tabs or electrically conductive adhesives. The power source 22 in combination with the electrodes 8 and 10 and the patient's body 6 completes the circuit and generates an electric field across the body surface or skin on which the iontophoretic device is applied. The electric field causes the drug in the active reservoir 14 to be delivered into the body of the patient by iontophoresis.

The lower surface of the reservoirs are placed in contact with the skin. The electrodes are positioned so that an electrical current path is established between the electrodes 8 and 10 through the reservoirs and the patient's skin 6. Electrodes 8 and 10 are placed in conductive contact with the gels of the reservoirs. A direct current source may be connected to the electrodes 8 and 10 so that the active electrode has the same charge polarity as the ionic drug 12. When current is passed through the active electrode 8 to the return electrode 10 and through the skin 6, the ionic drug 12 contained in the active reservoir 14 is delivered through the skin 6 and into the patient.

Figure 3:
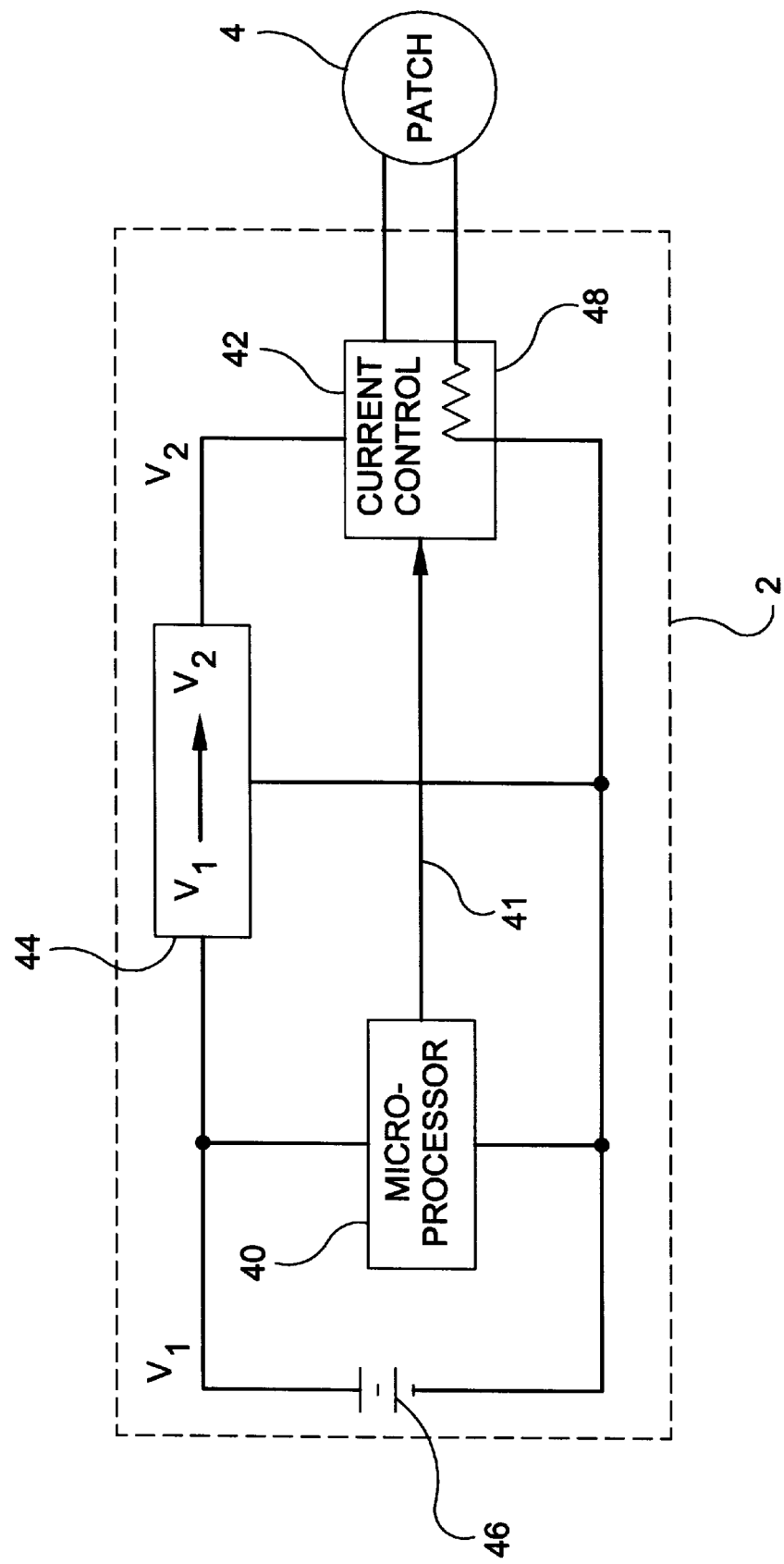
FIG. 3 is a block diagram of a iontophoretic controller circuit in accordance with the present invention.

FIG. 3 depicts a controller 2 that may include, but is not limited to, a microprocessor 40, a voltage converter 44, and a current control circuit 42. The voltage converter 44 converts a voltage V1 from the battery 46 to a different voltage V2. Of course, while the figure depicts a battery 46 as a stack of two cells, any number of cells may be used. The current control circuit is powered by the converted voltage V2. The microprocessor 40 may be powered directly by the battery voltage V1, as shown in FIG. 3. Alternatively, the microprocessor 40 may be powered by the converted voltage V2.

The microprocessor 40 sends a control signal 41 to the current control circuit 42. The microprocessor 40 can generate this control signal 41 by, for example, writing a digital word to an internal or an external analog-to-digital converter (not shown). Digital control signals may also be used in alternative embodiments. The control signal 41 commands the current control circuit to deliver a desired amount of current, corresponding to a particular dose of drug, to the patch 4. The current control circuit 42 will produce the required amount of output current irrespective of the varying impedance and/or capacitance of the load, including the patient's skin, the impedance of which normally varies from patient to patient and which may change as iontophoresis takes place. In order to drive the desired current into the patch 4, the current control circuit 42 will change the voltage it applies to the patch. When V2 is greater than V1, more current can be driven through the patch as compared to systems that do not use a voltage converter 44.

Voltage from a sensor, such as a current sense resistor 48, is monitored by the current control circuit 42 to ensure that the delivered current is correct. The current passing through the current sense resistor 48 is the same current actually being delivered through the iontophoretic patch and the skin. If the amount of current actually delivered is less than or greater than the required current, the current control circuit 42 adjusts the current to the required level by adjusting the voltage it applies to the patch.

Figure 4A:
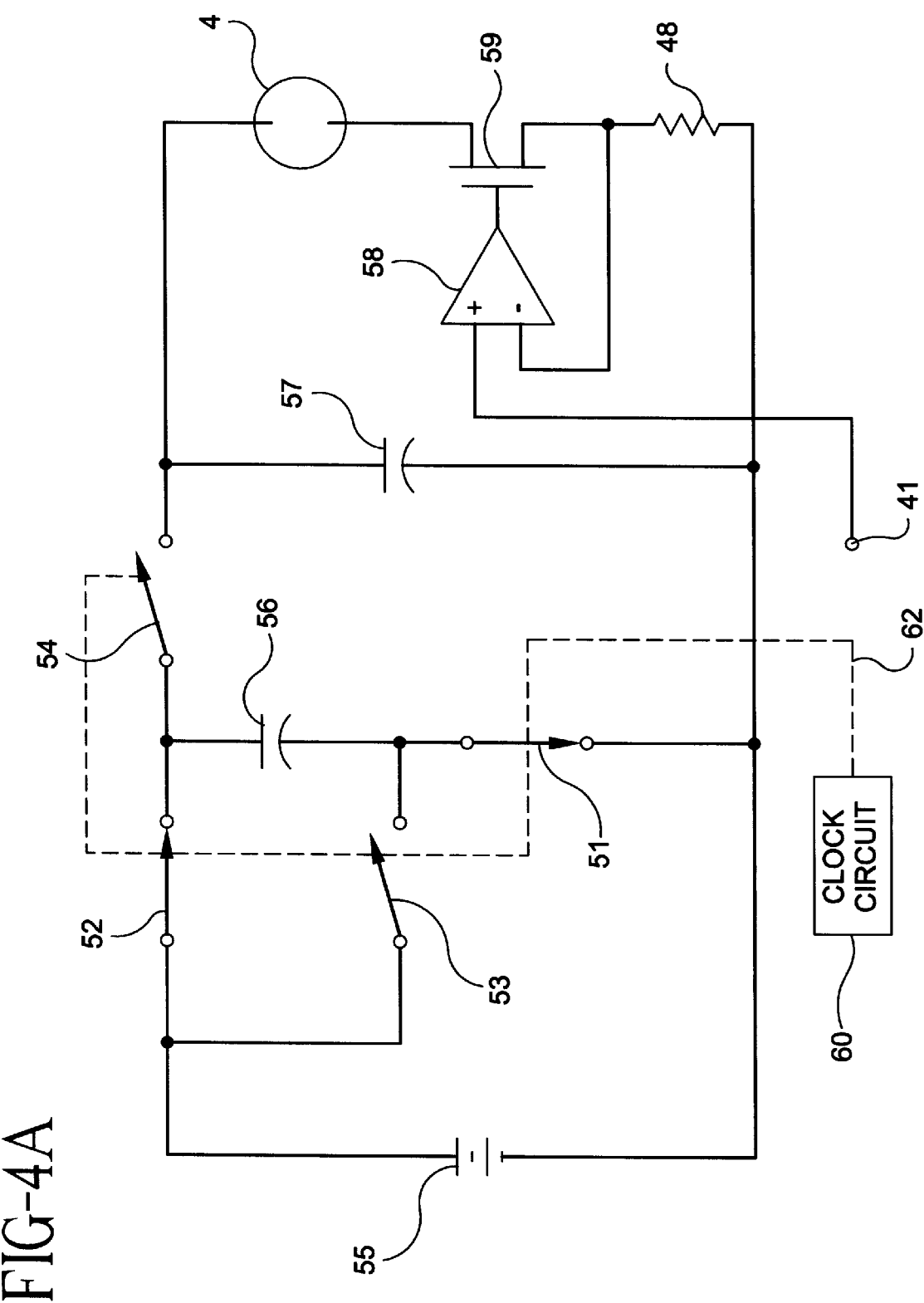
FIG. 4A is a schematic diagram of a first state of a voltage converter that may be used in the present invention.
Figure 4B:
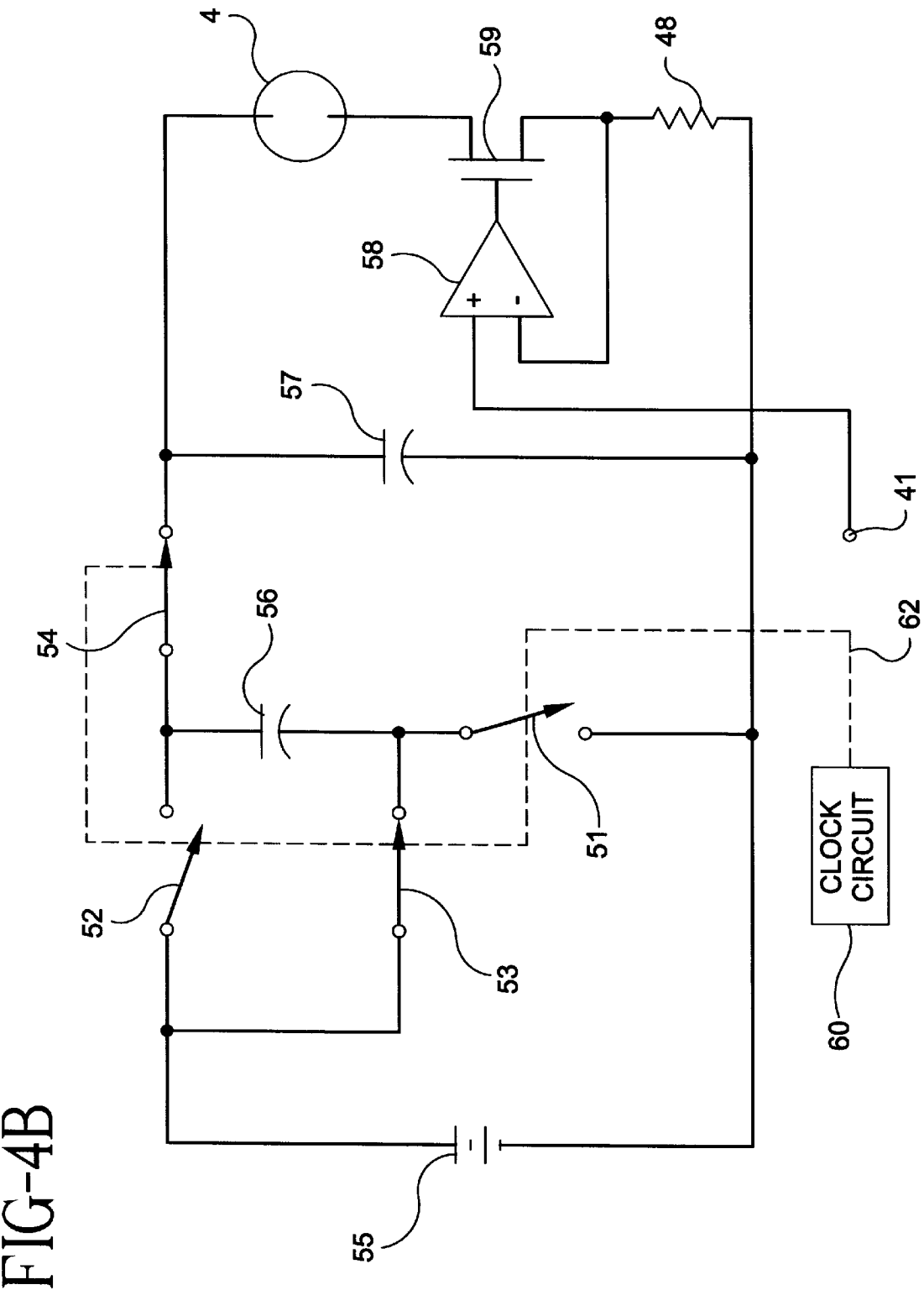
FIG. 4B is a schematic diagram of a second state of the voltage converter of FIG. 4A.

FIGS. 4A and 4B depict a preferred switched-capacitor DC—DC voltage converter (also known as a charge pump converter), for use in this invention. In this circuit, the switches 51, 52, 53, and 54 are electronically controlled switches that are controlled by an output of the clock circuit 60. These switches are preferably MOS transistor switches, the gates of which are controlled by digital logic level inputs. The control function is indicated by the dashed line 62 in FIGS. 4A and 4B. When the output of the clock circuit 60 is in its first state, the switches are in the state depicted in FIG. 4A. In this state, the switches 51 and 52 are closed, and the switches 53 and 54 are open. When the output of the clock circuit 60 is in its second state, the positions of each of the switches 51–54 are reversed so that switches 51 and 52 are open and switches 53 and 54 are closed.

In the first state, when switches 51 and 52 are closed, the voltage $V_{BAT}$ from the battery 55 is applied across the capacitor 56. The capacitor 56 charges up until the voltage across the capacitor 56 is equal to $V_{BAT}$. Because the switch 54 is open, no current flows out of the capacitor 56 toward the right side of the circuit.

When the clock 60 changes its state, the switches 51 and 52 open and the switches 53 and 54 close, as shown in FIG. 4B. In this state, the capacitor 56 is connected in series with the battery 55 through the switch 53. Because the capacitor is charged to $V_{BAT}$, the voltage across this series combination is $2V_{BAT}$. The series-connected combination of the battery 55 and the capacitor 56 is connected to the capacitor 57 through the switch 54.

As a result, the capacitor 57 charges up to almost $2V_{BAT}$. The capacitor 57 stores this doubled voltage which is then used by the current control circuit depicted to the right of the capacitor 57.

Because the clock circuit alternately generates ONEs and ZEROs in sequence, the operation of the left side of the circuit, described above, repeats continuously. This results in the doubled voltage $2V_{BAT}$ being maintained on the capacitor 57. While the current control circuit draws charge from the capacitor 57, the impact on the voltage of capacitor 57 will be small if the load current to the patch is sufficiently low.

Because most iontophoretic applications use low-level currents (typically 100–2000 $\mu$A), switched-capacitor DC—DC voltage converters will perform well. In addition, by using a switched-capacitor DC—DC voltage converter in accordance with this invention, the disadvantages of the transformer and inductor based DC—DC converters described above can be avoided.

The principle described above can be extended to triple or quadruple the battery voltage, or more, by switching more capacitors in series. Any integer multiple of the battery voltage can be obtained. Although not so depicted, non-integer multiple voltages can also be achieved by regulating down from a higher integer multiple of the battery voltage. For example, a voltage of $3.5V_{BAT}$ can be achieved by regulating down from $4V_{BAT}$.

Many other configurations of switched capacitor converters may be used instead of the circuit shown in FIGS. 4A and 4B. For example, instead of doubling the battery voltage from $V_{BAT}$ to $2V_{BAT}$ as described above, a unipolar input power voltage of $V_{BAT}$ may be converted to $\pm V_{BAT}$ by charging a capacitor up to $V_{BAT}$, and then switching the capacitor so that its positive terminal is connected to ground. The negative terminal of the capacitor can then be used as a $-V_{BAT}$ output, and the current control circuit can be powered from the $\pm V_{BAT}$ rails.

The right side of FIG. 4A depicts an iontophoretic current control circuit that runs from the stepped-up voltage. This circuit includes the field effect transistor (FET) 59, the current sensor resistor 48, and the operational amplifier (op amp) 58. A control signal is provided from the microprocessor 40 (shown in FIG. 3) to the positive input of the op amp 58. This control signal determines the desired patch current. The same current that flows through the patch 4 also flows through the FET 59 and the current sensor resistor 48. This current induces a voltage across the current resistor sense 48. When the patch current is lower than the desired current, the voltage induced across the resistor 48 is lower than the voltage at the control input 41. When this occurs, the output of the op amp 58 will rise. This causes the FET 59 to turn on harder, which increases the flow of current through the patch 4 and the current sensor resistor 48. The current through the current sense resistor 48 will rise until the induced voltage is equal to the voltage at the control input 41. At this point, the output of the op amp 58 will stabilize. If changing conditions in the patch 4 or the patient's skin cause the output current to deviate from the desired set point, the voltage across the current sense resistor 48 will change. Negative feedback to the op amp 58 will then move the output of the amp 58 until the output current is restored to the desired level.

The op amp 58 may be powered directly by the battery 55. Alternatively, the op amp 58 may be powered from the doubled voltage. Similarly, the microprocessor 40 (shown in FIG. 3) can also be powered from either the battery voltage 55 or from the doubled voltage.

Of course, it will be appreciated that the invention may take forms other than those specifically described. Some examples include replacing the microprocessor 40 that generates the control signal 41 with a state machine or an analog controller; replacing the FET 59 depicted with another type of transistor; and replacing the op amp 58 with another feedback circuit. Accordingly, while the preferred embodiments of the present invention have been described so as to enable one skilled in the art to practice the devices and methods of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. An apparatus for iontophoretic drug delivery, comprising:
    a controller having an output signal comprising;
    a switched capacitor DC—DC voltage converter with the capability for alternating between series and parallel connection to a voltage source and having an input for receiving an input voltage and a voltage converter output with an output voltage, the output voltage being greater than the input voltage; and
    a current control circuit connected to the switched capacitor DC—DC voltage converter for controlling an iontophoretic current drawn from the voltage converter output in accordance with the controller output signal.

2. The apparatus according to claim 1, further comprising an iontophoretic patch.

3. The apparatus according to claim 1, further comprising a battery that provides power to the voltage converter input.

4. The apparatus according to claim 1, wherein the controller is powered by the voltage converter output.

5. The apparatus according to claim 1 wherein the output voltage from the voltage converter is approximately double the input voltage.

6. The apparatus according to claim 1,
    wherein the voltage converter comprises a first capacitor and a second capacitor;
    the first capacitor is alternately switched in parallel to a battery in a first state to charge the first capacitor, and switched in series with the battery in a second state to produce a series voltage; and
    the series voltage is switched to charge the second capacitor during the second state.

7. A method of iontophoretic drug delivery, comprising the steps of:
    converting an input voltage to an output voltage greater than the input voltage using a switched capacitor DC—DC converter;
    controlling an iontophoretic current supplied from the output voltage; and
    supplying the iontophoretic current to an iontophoretic patch wherein the converting steps includes the steps of charging a first capacitor to the input voltage; switching the first capacitor so that it is in series with an input power source, thereby forming a series circuit; and switching a second capacitor in parallel with the series circuit.

8. The method according to claim 7, wherein the converting step includes the step of charging a capacitor to the output voltage.

9. The method according to claim 7, wherein the steps of switching the first capacitor and switching the second capacitor are performed together, and are alternated repeatedly with the step of charging the first capacitor.

10. The method according to claim 7, wherein the converting step converts the input voltage using at least two switched capacitor DC—DC converters.

* * * * *